United States Patent
Krivopisk et al.

(10) Patent No.: US 11,782,259 B2
(45) Date of Patent: Oct. 10, 2023

(54) CIRCUIT BOARD ASSEMBLY FOR A MULTIPLE VIEWING ELEMENTS ENDOSCOPE USING CMOS SENSORS

(71) Applicant: EndoChoice, Inc., Alpharetta, GA (US)

(72) Inventors: Leonid Krivopisk, Nesher (IL); Amram Aizenfeld, Ramot Menashe (IL); Golan Salman, Atlit (IL)

(73) Assignee: EndoChoice, Inc., Alpharetta, GA (US)

( * ) Notice: Subject to any disclaimer, the term of this patent is extended or adjusted under 35 U.S.C. 154(b) by 0 days.

(21) Appl. No.: 17/133,307

(22) Filed: Dec. 23, 2020

(65) Prior Publication Data
US 2021/0116697 A1   Apr. 22, 2021

Related U.S. Application Data

(63) Continuation of application No. 16/654,612, filed on Oct. 16, 2019, now Pat. No. 10,908,407, which is a
(Continued)

(51) Int. Cl.
*G02B 23/24* (2006.01)
*A61B 1/00* (2006.01)
(Continued)

(52) U.S. Cl.
CPC ........ *G02B 23/2484* (2013.01); *A61B 1/0011* (2013.01); *A61B 1/00181* (2013.01);
(Continued)

(58) Field of Classification Search
CPC ............ G02B 23/2484; G02B 23/2423; G02B 23/2461; A61B 1/0011; A61B 1/00181; A61B 1/00188; A61B 1/05; A61B 1/051; A61B 1/0676; A61B 1/0684; A61B 1/00177; A61B 1/00197; H04N 5/2256;
(Continued)

(56) References Cited

U.S. PATENT DOCUMENTS

| | | |
|---|---|---|
| 3,639,714 A | 2/1972 | Fujimoto |
| 3,955,064 A | 5/1976 | Demetrio |

(Continued)

FOREIGN PATENT DOCUMENTS

| | | |
|---|---|---|
| CA | 2297986 | 3/1999 |
| CA | 2765559 | 12/2010 |

(Continued)

OTHER PUBLICATIONS

Notice of Allowance dated Apr. 12, 2017 for U.S. Appl. No. 14/603,137.
(Continued)

*Primary Examiner* — Nasim N Nirjhar
(74) *Attorney, Agent, or Firm* — Bookoff McAndrews, PLLC

(57) ABSTRACT

A circuit board design uses CMOS sensors for the tip section of a multi-viewing element endoscope. Side sensors and their optical assemblies are assembled to a common base board to save space. Individual base boards are separately constructed, inserted into grooves of a main base board, and are further connected to the main base board by means of flexible circuit boards.

19 Claims, 14 Drawing Sheets

Related U.S. Application Data continuation of application No. 15/435,580, filed on Feb. 17, 2017, now Pat. No. 10,488,648.

(60) Provisional application No. 62/299,332, filed on Feb. 24, 2016.

(51) Int. Cl.
| | |
|---|---|
| *A61B 1/06* | (2006.01) |
| *A61B 1/05* | (2006.01) |
| *H04N 23/45* | (2023.01) |
| *H04N 23/56* | (2023.01) |
| *H04N 25/76* | (2023.01) |
| *H04N 23/50* | (2023.01) |

(52) U.S. Cl.
CPC ............ *A61B 1/00188* (2013.01); *A61B 1/05* (2013.01); *A61B 1/051* (2013.01); *A61B 1/0676* (2013.01); *A61B 1/0684* (2013.01); *G02B 23/2423* (2013.01); *G02B 23/2461* (2013.01); *H04N 23/45* (2023.01); *H04N 23/56* (2023.01); *H04N 25/76* (2023.01); *A61B 1/00177* (2013.01); *A61B 1/00197* (2013.01); *H04N 23/555* (2023.01)

(58) Field of Classification Search
CPC ................. H04N 5/2258; H04N 5/374; H04N 2005/2255
See application file for complete search history.

(56) References Cited

U.S. PATENT DOCUMENTS

| | | | |
|---|---|---|---|
| 4,027,697 A | 6/1977 | Bonney | |
| 4,037,588 A | 7/1977 | Heckele | |
| 4,084,401 A | 4/1978 | Belardi | |
| 4,241,381 A * | 12/1980 | Cobaugh | H05K 7/1457 |
| | | | 361/624 |
| 4,402,313 A | 9/1983 | Yabe | |
| 4,461,282 A | 7/1984 | Ouchi | |
| 4,494,549 A | 1/1985 | Namba | |
| 4,532,918 A | 8/1985 | Wheeler | |
| 4,588,294 A | 5/1986 | Siegmund | |
| 4,641,635 A | 2/1987 | Yabe | |
| 4,727,859 A | 3/1988 | Lia | |
| 4,764,001 A | 8/1988 | Yokota | |
| 4,801,792 A | 1/1989 | Yamasita | |
| 4,825,850 A | 5/1989 | Opie | |
| 4,877,314 A | 10/1989 | Kanamori | |
| 4,902,115 A | 2/1990 | Takahashi | |
| 4,976,522 A | 12/1990 | Igarashi | |
| 4,984,878 A | 1/1991 | Miyano | |
| 5,007,406 A | 4/1991 | Takahashi | |
| 5,014,685 A | 5/1991 | Takahashi | |
| 5,193,525 A | 3/1993 | Silverstein | |
| 5,200,818 A | 4/1993 | Neta | |
| 5,224,929 A | 7/1993 | Remiszewski | |
| 5,296,971 A | 3/1994 | Mori | |
| 5,359,456 A | 10/1994 | Kikuchi | |
| 5,395,329 A | 3/1995 | Fleischhacker | |
| 5,447,148 A | 9/1995 | Oneda | |
| 5,460,167 A | 10/1995 | Yabe | |
| 5,464,007 A | 11/1995 | Krauter | |
| 5,468,156 A | 11/1995 | Flinchbaugh | |
| 5,475,420 A | 12/1995 | Buchin | |
| 5,489,256 A | 2/1996 | Adair | |
| 5,518,501 A | 5/1996 | Oneda | |
| 5,518,502 A | 5/1996 | Kaplan | |
| 5,547,455 A | 8/1996 | McKenna | |
| 5,547,457 A | 8/1996 | Tsuyuki | |
| 5,575,755 A | 11/1996 | Krauter | |
| 5,587,839 A | 12/1996 | Miyano | |
| 5,630,782 A | 5/1997 | Adair | |
| 5,630,798 A | 5/1997 | Beiser | |
| 5,662,588 A | 9/1997 | Iida | |
| 5,674,182 A | 10/1997 | Suzuki | |
| 5,685,821 A | 11/1997 | Pike | |
| 5,685,823 A | 11/1997 | Ito | |
| 5,702,347 A | 12/1997 | Yabe | |
| 5,707,344 A | 1/1998 | Nakazawa | |
| 5,725,474 A | 3/1998 | Yasui | |
| 5,725,476 A | 3/1998 | Yasui | |
| 5,725,477 A | 3/1998 | Yasui | |
| 5,725,478 A | 3/1998 | Saad | |
| 5,777,797 A | 7/1998 | Miyano | |
| 5,782,751 A | 7/1998 | Matsuno | |
| 5,800,341 A | 9/1998 | McKenna | |
| 5,810,715 A | 9/1998 | Moriyama | |
| 5,810,717 A | 9/1998 | Maeda | |
| 5,810,770 A | 9/1998 | Chin | |
| 5,812,893 A | 9/1998 | Hikita | |
| 5,830,121 A | 11/1998 | Enomoto | |
| 5,836,894 A | 11/1998 | Sarvazyan | |
| 5,860,913 A | 1/1999 | Yamaya | |
| 5,870,234 A | 2/1999 | EbbesmeierneeSchitthof | |
| 5,916,148 A | 6/1999 | Tsuyuki | |
| 5,940,126 A | 8/1999 | Kimura | |
| 6,058,109 A | 5/2000 | Lechleider | |
| 6,095,970 A | 8/2000 | Hidaka | |
| 6,095,971 A | 8/2000 | Takahashi | |
| 6,117,068 A | 9/2000 | Gourley | |
| 6,181,481 B1 | 1/2001 | Yamamoto | |
| 6,196,967 B1 | 3/2001 | Lim | |
| 6,261,226 B1 | 7/2001 | McKenna | |
| 6,277,064 B1 | 8/2001 | Yoon | |
| 6,359,674 B1 | 3/2002 | Horiuchi | |
| 6,375,610 B2 | 4/2002 | Verschuur | |
| 6,402,738 B1 | 6/2002 | Ouchi | |
| 6,419,626 B1 | 7/2002 | Yoon | |
| 6,450,950 B2 | 9/2002 | Irion | |
| 6,476,851 B1 | 11/2002 | Nakamura | |
| 6,520,908 B1 | 2/2003 | Ikeda | |
| 6,636,254 B1 | 10/2003 | Onishi | |
| 6,638,214 B2 | 10/2003 | Akiba | |
| 6,673,012 B2 | 1/2004 | Fujii | |
| 6,690,337 B1 | 2/2004 | Mayer, III | |
| 6,712,760 B2 | 3/2004 | Sano | |
| 6,764,345 B1 | 7/2004 | Duesterhoeft | |
| 6,814,583 B1 | 11/2004 | Young | |
| 6,832,964 B2 | 12/2004 | Stetzer | |
| 6,888,119 B2 | 5/2005 | Iizuka | |
| 6,997,871 B2 | 2/2006 | Sonnenschein | |
| 7,154,378 B1 | 12/2006 | Ertas | |
| 7,268,805 B2 | 9/2007 | Yoshikawa | |
| 7,435,218 B2 | 10/2008 | Krattiger | |
| 7,621,869 B2 | 11/2009 | Ratnakar | |
| 7,630,148 B1 | 12/2009 | Yang | |
| 7,701,650 B2 | 4/2010 | Lin | |
| 7,713,246 B2 | 5/2010 | Shia | |
| 7,746,572 B2 | 6/2010 | Asami | |
| 7,796,870 B2 | 9/2010 | Wang | |
| 7,813,047 B2 | 10/2010 | Wang | |
| 7,828,725 B2 | 11/2010 | Maruyama | |
| 7,918,788 B2 | 4/2011 | Lin | |
| 7,927,272 B2 | 4/2011 | Bayer | |
| 7,967,745 B2 | 6/2011 | Gilad | |
| 7,976,462 B2 | 7/2011 | Wright | |
| 8,064,666 B2 | 11/2011 | Bayer | |
| 8,182,422 B2 | 5/2012 | Bayer | |
| 8,197,399 B2 | 6/2012 | Bayer | |
| 8,235,887 B2 | 8/2012 | Bayer | |
| 8,262,558 B2 | 9/2012 | Sato | |
| 8,287,446 B2 | 10/2012 | Bayer | |
| 8,289,381 B2 | 10/2012 | Bayer | |
| 8,300,325 B2 | 10/2012 | Katahira | |
| 8,310,530 B2 | 11/2012 | Bayer | |
| 8,353,860 B2 | 1/2013 | Boulais | |
| 8,447,132 B1 | 5/2013 | Galil | |
| 8,449,457 B2 | 5/2013 | Aizenfeld | |
| 8,460,182 B2 | 6/2013 | Ouyang | |
| 8,585,584 B2 | 11/2013 | Ratnakar | |
| 8,587,645 B2 | 11/2013 | Bayer | |
| 8,672,836 B2 | 3/2014 | Higgins | |

(56) References Cited

U.S. PATENT DOCUMENTS

| | | |
|---|---|---|
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,185,391 B1 | 11/2015 | Prechtl |
| 9,289,110 B2 | 3/2016 | Woolford |
| 9,314,147 B2 | 4/2016 | Levy |
| 9,320,419 B2 | 4/2016 | Kirma |
| 9,407,819 B2 | 8/2016 | Guissin |
| 9,615,011 B1 | 4/2017 | Fleming |
| 9,690,172 B2 | 6/2017 | Donaldson |
| 9,838,599 B1 | 12/2017 | Tam |
| 10,186,301 B1 | 1/2019 | Van Hoff |
| 10,488,648 B2 | 11/2019 | Krivopisk et al. |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0114622 A1 | 5/2005 | Bungo |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0267328 A1 | 12/2005 | Blumzvig |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188127 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | DeLorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021270 A1 | 1/2008 | Suzushima |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | ONeal |
| 2008/0253686 A1 | 10/2008 | Bayer |
| 2008/0262312 A1 | 10/2008 | Carroll |
| 2008/0275298 A1 | 11/2008 | Ratnakar |
| 2008/0298674 A1 | 12/2008 | Baker |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |

(56) References Cited

U.S. PATENT DOCUMENTS

| | | |
|---|---|---|
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245539 A1 | 9/2010 | Lin |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0084835 A1 | 4/2011 | Whitehouse |
| 2011/0128393 A1 | 6/2011 | Tavi |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0142381 A1 | 5/2014 | Bae |
| 2014/0148644 A1 | 5/2014 | Levi |
| 2014/0173140 A1 | 6/2014 | Bates |
| 2014/0184766 A1 | 7/2014 | Amling |
| 2014/0213850 A1 | 7/2014 | Levy |
| 2014/0225998 A1 | 8/2014 | Dai |
| 2014/0253678 A1 | 9/2014 | Tocher |
| 2014/0276207 A1 | 9/2014 | Ouyang |
| 2014/0296628 A1 | 10/2014 | Kirma |
| 2014/0296643 A1* | 10/2014 | Levy ..................... A61B 1/051 |
| | | 600/160 |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099926 A1 | 4/2015 | Davidson |
| 2015/0105618 A1 | 4/2015 | Levy |
| 2015/0116453 A1 | 4/2015 | Hirata |
| 2015/0138311 A1 | 5/2015 | Towndrow |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0206900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0264232 A1 | 9/2015 | Yang |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |
| 2016/0142692 A1 | 5/2016 | Kim |
| 2016/0174998 A1* | 6/2016 | Lal ........................ A61B 5/685 |
| | | 606/169 |
| 2016/0309992 A1 | 10/2016 | Stith |

(56) References Cited

U.S. PATENT DOCUMENTS

2017/0023492 A1 1/2017 Olsson
2017/0325665 A1 11/2017 Krivopisk
2017/0325669 A1 11/2017 Levy

FOREIGN PATENT DOCUMENTS

| | | |
|---|---|---|
| CA | 2812097 | 3/2012 |
| CA | 2770661 A1 | 9/2012 |
| CA | 2798716 | 6/2013 |
| CA | 2798729 | 6/2013 |
| CN | 103070660 A | 5/2013 |
| CN | 103348470 | 10/2013 |
| CN | 103403605 | 11/2013 |
| CN | 103491854 | 1/2014 |
| CN | 103732120 | 4/2014 |
| CN | 103792604 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| DE | 102011115500 A1 | 4/2013 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211883 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2649648 | 10/2013 |
| EP | 26548602 | 10/2013 |
| EP | 2672878 | 12/2013 |
| EP | 2744390 | 6/2014 |
| EP | 2736400 | 8/2014 |
| EP | 2442706 | 11/2014 |
| EP | 2865322 | 4/2015 |
| EP | 2908714 | 8/2015 |
| EP | 2991537 | 3/2016 |
| EP | 2994032 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| EP | 2979123 | 2/2018 |
| EP | 2994033 | 3/2018 |
| GB | 12196628 | 3/2015 |
| JP | 04341232 A | 11/1992 |
| JP | H1043129 | 2/1998 |
| JP | 10179516 A | 7/1998 |
| JP | H10239740 | 9/1998 |
| JP | 11137512 | 5/1999 |
| JP | 2004134875 A | 4/2004 |
| JP | 3645055 B2 | 5/2005 |
| JP | 2005253543 | 9/2005 |
| JP | 2006025888 | 2/2006 |
| JP | 2006968109 | 3/2006 |
| JP | 2010012079 A | 1/2010 |
| JP | 2010178766 A | 8/2010 |
| JP | 2011082215 A | 4/2011 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013514617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 A1 | 12/2010 |
| WO | 2012038958 | 3/2012 |
| WO | 2012056453 A2 | 5/2012 |
| WO | 2012075153 A2 | 6/2012 |
| WO | 2012077117 A1 | 6/2012 |
| WO | 2612077116 | 6/2012 |
| WO | 2012096102 | 7/2012 |
| WO | 2012120507 A1 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | WO 2014203604 A1 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | WO 2015151973 A1 | 10/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2018 |
| WO | WO 2018135261 A1 | 7/2018 |

OTHER PUBLICATIONS

Notice of Allowance dated Apr. 18, 2017 for U.S. Appl. No. 13/713,449.
Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/27,270.
Office Action dated May 15, 2017 for U.S. Appl. No. 14/278,293.

(56) References Cited

OTHER PUBLICATIONS

Office Action dated May 18, 2017 for U.S. Appl. No. 14/278,338.
Notice of Allowance dated May 16, 2017 for U.S. Appl. No. 14/746,986.
Office Acton dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.
International Search Repost for PCTU14/37004, dated Sep. 25, 2014.
International Search Report for PCT/US14/38094, dated Nov. 6, 2014.
International Search Report for PCT/US2014/037526, dated Oct. 16, 2014.
International Search Report for PCT/US2014/071085, dated Mar. 27, 2015.
International Search Report for PCT/US2014/58143, dated Jan. 21, 2015.
International Search Report for PCT/US2015/012506, dated Dec. 11, 2015.
International Search Report for PCT/US2015/012751, dated Jun. 26, 2015.
International Search Report for PCT/US2015/027902, dated Jul. 23, 2015.
International Search Report for PCT/US2015/28962, dated Jul. 28, 2015.
International Search Report for PCT/US2015/29421, dated Aug. 7, 2015.
International Search Report for PCT/US2015/41396, dated Sep. 29, 2015.
International Search Report for PCT/US2015/47334, dated Dec. 28, 2015.
International Search Report for PCT/US2015/6548, dated Feb. 26, 2016.
International Search Report for PCT/US2015/664686, dated Dec. 17, 2015.
International Search Report for PCT/US2017/018287, dated May 10, 2017.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Feb. 26, 2016 for U.S. Appl. No. 14/274,323.
Office Action dated Feb. 4, 2016 for U.S. Appl. No. 14/271,234.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
Office Action dated Jun. 30, 2016 for U.S. Appl. No. 13/655,120.
Office Action dated Jun. 28, 2018 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Alllowance dated Jul. 15, 2016 for U.S. Appl. No. 14/274,323.
Office Action dated Jul. 22, 2016 for U.S. Appl. No. 14/549,265.
Sherman L. M., Plastics That Conduct Heat, Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2015 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 26, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Offive Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.

\* cited by examiner

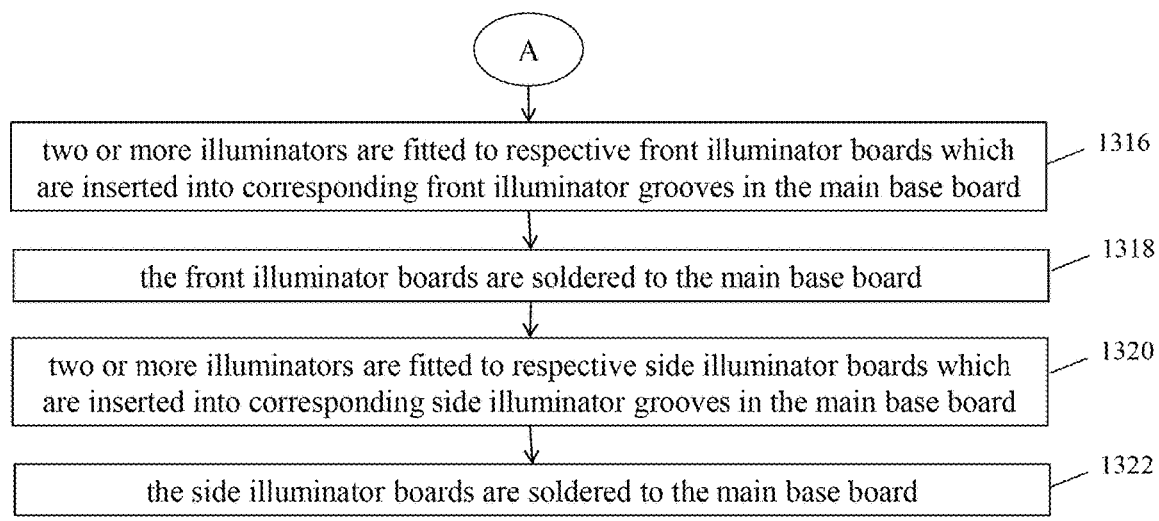
FIG. 13 contd.

CIRCUIT BOARD ASSEMBLY FOR A MULTIPLE VIEWING ELEMENTS ENDOSCOPE USING CMOS SENSORS

CROSS-REFERENCE

This application is a continuation of U.S. Nonprovisional patent application Ser. No. 16/654,612, filed Oct. 16, 2019, which is a continuation of U.S. Nonprovisional patent application Ser. No. 15/435,580, filed Feb. 17, 2017, now U.S. Pat. No. 10,488,648, issued Nov. 26, 2019, which claims the benefit of U.S. Provisional Patent Application No. 62/299,332, filed on Feb. 24, 2016.

The present application relates to U.S. patent application Ser. No. 14/469,481, filed on Aug. 26, 2014, which relies on U.S. Provisional Patent No. 61/987,984, filed on May 2, 2014; U.S. Provisional Patent No. 61/935,647, filed on Feb. 4, 2014, and U.S. Provisional Patent No. 61/881,661, filed on Sep. 24, 2013, for priority.

The present application also relates to U.S. patent application Ser. No. 13/882,004, filed on May 23, 2013, which is a 371 National Stage Entry of PCT Application No. PCT/IL2011/000832, filed on Oct. 27, 2011, which, relies upon U.S. Provisional Patent Application No. 61/407,495, filed on Oct. 28, 2010, for priority.

The present specification also relates to U.S. patent application Ser. No. 13/992,014, filed on Jun. 6, 2013, which is a 371 National Stage Entry of PCT Application No. PCT/IL2011/050049, filed on Dec. 8, 2011, which relies upon U.S. Provisional Patent Application No. 61/421,238, filed on Dec. 9, 2010, for priority.

The present specification also relates to U.S. patent application Ser. No. 13/992,021, filed on Jun. 6, 2013, which is a 371 National Stage Entry of PCT Application No. PCT/IL2011/050050, filed on Dec. 8, 2011, which relies upon U.S. Provisional Patent Application No. 61/421,240, filed on Dec. 9, 2010, for priority.

The present application also relates to the following U.S. patent applications:

U.S. patent application Ser. No. 13/655,120, filed on Oct. 18, 2012; U.S. patent application Ser. No. 13/212,627, filed on Aug. 18, 2011; and U.S. patent application Ser. No. 14/746,986, filed on Jan. 21, 2016, which is a continuation of U.S. Pat. No. 9,101,268, issued on Aug. 11, 2015, all of which are continuation-in-part applications of U.S. patent application Ser. No. 13/119,032, filed on Jul. 15, 2011, which is a 371 National Stage Entry of PCT Application No. PCT/IL2010/000476, filed on Jun. 16, 2010, which relies upon U.S. Provisional Patent Application No. 61/218,085, for priority.

All of the above-mentioned applications are herein incorporated by reference in their entirety.

FIELD

The present specification relates generally to endoscopes, and more specifically, to a circuit board assembly for the tip section of a multiple viewing element endoscope that uses CMOS image sensors for capturing images.

BACKGROUND

Endoscopes have attained great acceptance within the medical community, since they provide a means for performing procedures, while enabling the physician to view the internal anatomy of the patient. Over the years, numerous endoscopes have been developed and categorized according to use in specific applications, such as cystoscopy, colonoscopy, laparoscopy, upper GI endoscopy among others. Endoscopes may be inserted into the body's natural orifices or through an incision in the skin.

An endoscope typically comprises an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

One disadvantage of existing endoscopes is their limited field of view. A limited field of view may not allow a physician to analyze an area under inspection in full detail. This in turn affects the rate of detection of pathological objects that exist in the body cavity in which the endoscope operates. For example, clinical literature shows that the average adenoma miss rate is over 24%. That is, detection of cancer is missed in more than 24 of every 100 patients. Further, from a medical industry viewpoint, unless a physician is correctly identifying cancer in at least 20% of cancer patients, the average miss rate is considered higher than industry. Therefore, there is a need in the art for endoscopes that allow a broader field of view. One approach to achieving this purpose is described in U.S. Patent Application No. 2011/0263938, which describes the use of multiple cameras or viewing elements in a single endoscope and is incorporated herein by reference.

In most embodiments of multi-camera endoscopes, CCD sensors are used as imagers in the circuit board assembly of the endoscope tip. As known in the art, CCD sensors generate analog signals while CMOS sensors generate digital signals. In a CCD sensor, every pixel's charge is transferred through a limited number of output nodes, often just one, to be converted to voltage, buffered, and sent off-chip as an analog signal. In a CMOS sensor on the other hand, each pixel has its own charge-to-voltage conversion, and the sensor often also includes amplifiers, noise-correction, and digitization circuits, so that the chip outputs digital signals. With each pixel doing its own conversion, each pixel can be accessed concurrently, thereby allowing high total bandwidth and high speed. Thus, while a CCD interface is analog and requires synchronization signals and more circuitry at the end point, CMOS is only driven by power input and generates high speed digital video interface. The use of CCD sensors requires electronics for digitizing pixels and for image processing, while CMOS sensors already contain the main blocks for digitization in the chip and require only software based processing for the images. CMOS sensor technology in recent years has leapfrogged CCDs owing to better performance, and the cost of CMOS sensors has become much lower due to a more advanced production process.

Therefore, there is a need in the art to simplify the electrical interface of the circuit board assembly used in the tip of multi viewing element endoscopes, such that it can employ CMOS sensors and support a digital interface. Such endoscopes would allow for easy control of the imagers as well as the image processing technique, while also providing a broader field of view compared to conventional single imager endoscopes. There is also need for a method of assembling CMOS sensors in the tip of multiple viewing element endoscopes so as to occupy minimum space in the limited space environment of the tip section.

SUMMARY

The present specification describes a circuit board design that uses CMOS sensors within the tip section of a multiple viewing elements endoscope. In one embodiment, sensors and optical assemblies, associated with at least one side viewing element, are assembled on a common base board. In another embodiment, a dedicated base board is provided for each of the front and side sensors and their corresponding optical assemblies. The individual base boards are connected to the main base board by means of flexible circuit boards.

The present specification discloses a circuit board assembly for use in a tip section of a multi-viewing element endoscope, said tip comprising a front pointing viewing element and at least one side pointing viewing element, wherein each viewing element comprises an image sensor and a lens assembly, said circuit board assembly comprising: a first base board to which the front pointing viewing element is connected; a second base board, wherein the at least one side pointing viewing element is connected to a first side of the second base board; and a third base board to which said first and said second base boards are connected, wherein said first and said second base boards are placed perpendicular to said third base board.

Optionally, the tip section comprises a second side pointing viewing element facing a direction opposite to the at least one side pointing viewing element, wherein the second side pointing viewing element is connected to a second side of the second base board and wherein the first side of the second base board is opposite the second side of the second base board.

Optionally, each image sensor is a CMOS sensor comprising a first optics portion coupled with a second chip portion having a plurality of connector pins.

Optionally, the second chip portion of the CMOS sensor is connected to the first side of the second base board or the second side of the second base board by said plurality of connector pins.

Optionally, said first and said second base boards are positioned perpendicular to each other.

Optionally, said first base board is coupled to a metal frame which is configured to hold the lens assembly of the front pointing viewing element.

Optionally, said second base board is coupled to at least one metal frame, wherein the metal frame is configured to hold the at least one side lens assembly. Optionally, said metal frame is configured as heat sinks.

Optionally, each of the front and side pointing viewing elements is associated with at least one illuminator, and wherein said circuit board assembly comprises a separate circuit board to hold each of the at least one illuminators.

Optionally, said third base board comprises grooves adapted to receive said first base board and said second base board.

The present specification also discloses a circuit board assembly for the tip of a multi-viewing element endoscope, said tip comprising a front pointing viewing element, a first side pointing viewing element, and a second side pointing viewing element, wherein each viewing element comprises an image sensor and a lens assembly, said circuit board assembly comprising: a first base board to which the front pointing viewing element is connected; a second base board to which a first side pointing viewing element is connected; a third base board to which a second side pointing viewing element is connected; and, a fourth base board having three grooves, wherein each of said three grooves are adapted to receive one of said first, second and third base boards and wherein each of said first, second and third base boards are placed perpendicular to said fourth base board.

Optionally, each image sensor is a CMOS sensor.

Optionally, each of said first, second and third base boards is further connected to said fourth base board by a flexible circuit board.

Optionally, said second and said third base boards are positioned parallel to each other.

Optionally, said second and said third base boards are positioned perpendicular to the first base board.

Optionally, the circuit board assembly further comprises a front illuminator circuit board.

Optionally, said front illuminator circuit board is shaped as a "U" and is configured to hold three illuminators associated with the front pointing viewing element.

Optionally, the circuit board assembly further comprises two side illuminator circuit boards.

Optionally, each of the two side illuminator circuit boards is shaped as a "U" and is configured to hold two illuminators associated with the first side pointing viewing element and the second side pointing viewing element.

Optionally, the length of the front illuminator circuit board ranges from 5.5 mm to 11.5 mm and the height of the front illuminator circuit board ranges from 2.0 mm to 8.5 mm.

Optionally, the length of each of the side illuminator circuit boards ranges from 5.5 mm to 11.5 mm and the height of each of the side illuminator circuit boards ranges from 1.0 mm to 7.5 mm.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 6b is a front view of an exemplary CMOS image sensor comprising an image sensor contact area, shown in FIG. 6a;

DETAILED DESCRIPTION

In one embodiment, the present specification discloses a circuit board design for the tip of an endoscope system that uses CMOS sensors as imagers. The circuit board design not only makes more efficient use of the space inside the distal tip, which is crowded with components, but also reduces the cost of the assembly and makes the design easier to scale compared to existing circuit board designs for multiple viewing element endoscopes. With the use of CMOS sensors, digital signals are obtained directly from the sensors and the endoscope system is not limited to the signal processing method directed by the sensor chipset, as is the case where CCD sensors are used. Thus, with the use of CMOS sensors, any image processing technique may be employed that is suitable for the specific clinical environment in which the endoscope is used. Further, the attributes of imagers, such as exposure time, integration time, frame rate and multi-camera synchronization can be more readily controlled along with the image processing. As CMOS sensors support high bandwidth, high resolution images can be generated during endoscopic procedures.

In an embodiment, the present specification provides a circuit board assembly to be fitted within a tip section of a multi-viewing endoscope, wherein the circuit board assembly is capable of accommodating both CCD and CMOS sensors. The use of CMOS sensors within endoscopes allows for easier control of the imagers as well as the image processing technique.

Figure 8:
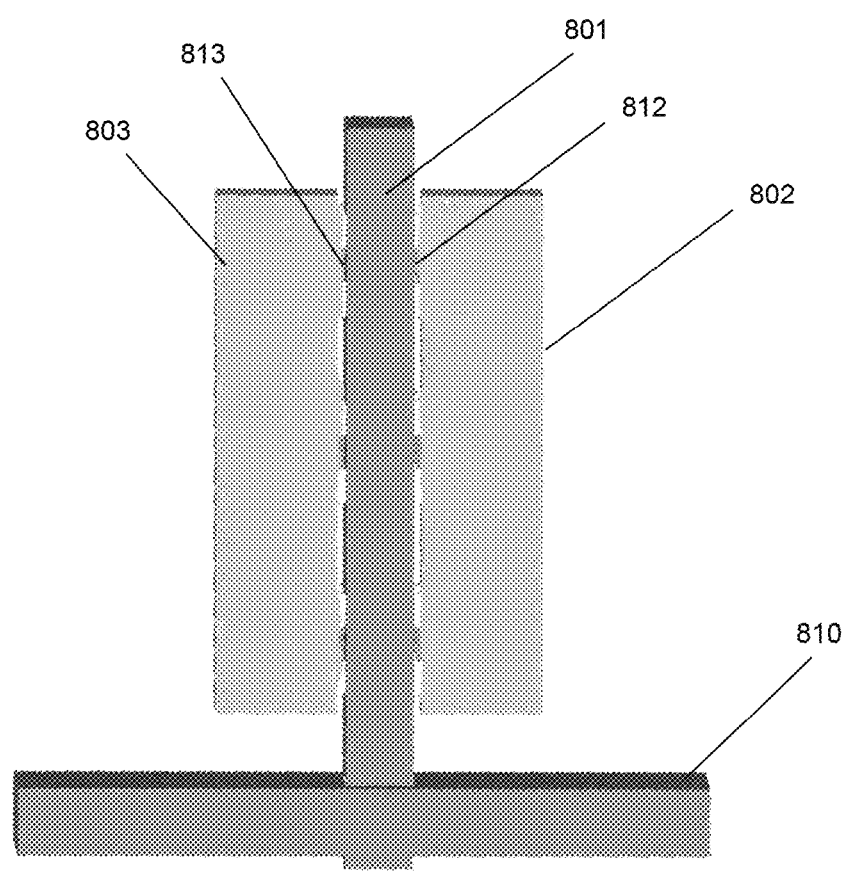
FIG. 8 illustrates another perspective view of the circuit board design, according to one embodiment of the present specification.

In another embodiment of the present specification, a circuit board assembly comprising one or more front and side facing CMOS sensors is provided for fitting into a tip section of a multi-viewing endoscope, providing a broader field of view compared to conventional single imager endoscopes. The circuit board assembly comprises two CMOS sensors connected to a single base board for conserving space in the tip section (as shown in FIG. 8).

Figure 9:
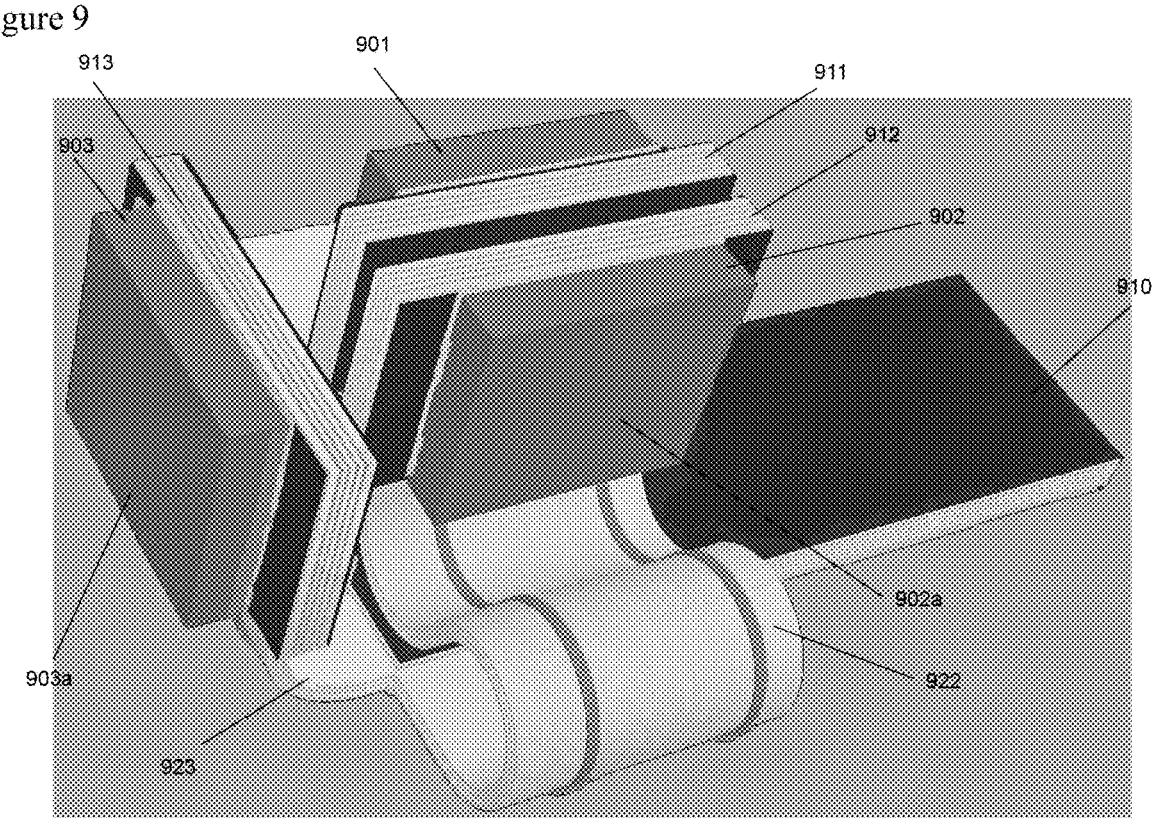
FIG. 9 illustrates another exemplary design of the base board assembly with CMOS sensors, according to one embodiment of the present specification.

In another embodiment, the present specification provides a circuit assembly comprising three CMOS sensors, each being connected to a separate base board, and each base board being connected to a main base board by means of a dedicated flexible circuit board or flex board (as shown in FIG. 9). The use of a flex board is advantageous in a multi-viewing element endoscope, given the shortage of space in the tip as a result of the presence of multiple viewing elements. The flex board provides additional freedom of movement to the assembly process in a space constrained environment.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

Figure 1:
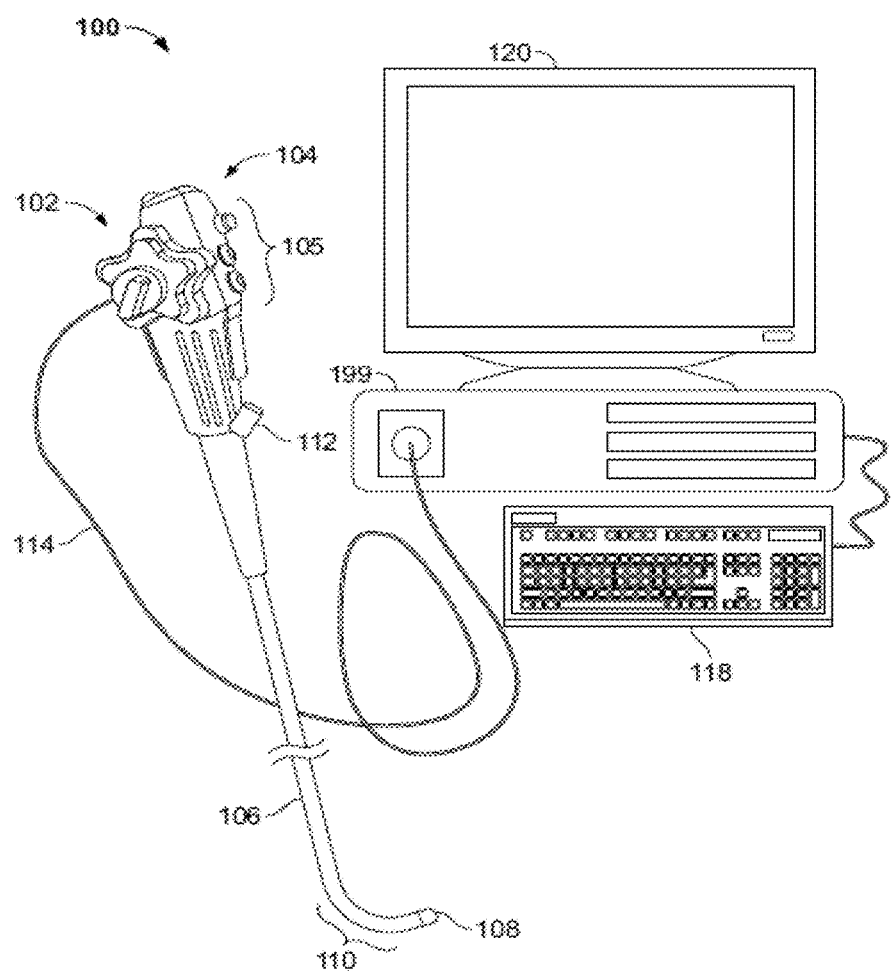
FIG. 1 illustrates a multiple viewing element endoscopy system.

Reference is now made to FIG. 1, which shows a multiple viewing element endoscopy system 100. System 100 may include a multiple viewing element endoscope 102. Multiple viewing element endoscope 102 may include a handle 104, from which an elongated shaft 106 emerges. Elongated shaft 106 terminates with a tip section 108 which is turnable by way of a bending section 110. Handle 104 may be used for maneuvering elongated shaft 106 within a body cavity. The handle may include one or more buttons and/or knobs and/or switches 105 which control bending section 110 as well as functions such as fluid injection and suction. Handle 104 may further include at least one, and in some embodiments, one or more working channel openings 112 through which surgical tools may be inserted as well as one and more side service channel openings.

A utility cable 114, also referred to as an umbilical tube, may connect between handle 104 and a Main Control Unit 199. Utility cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s) which supply corresponding functionalities to the endoscope 102. One or more input devices 118, such as a keyboard, a touch screen, a voice controller and the like may be connected to the main control unit 199 for the purpose of user interaction with the main control unit 199. In the embodiment shown in FIG. 1, the main control unit 199 comprises a screen/display 120 for displaying operation information concerning an endoscopy procedure when the endoscope 102 is in use. The screen 120 may be configured to display images and/or video streams received from the viewing elements of the multi-viewing element endoscope 102. The screen 120 may further be operative to display a user interface for allowing a human operator to set various features of the endoscopy system.

Optionally, the video streams received from the different viewing elements of the multi-viewing element endoscope 102 may be displayed separately on at least one monitor (not seen) by uploading information from the main control unit 199, either side-by-side or interchangeably (namely, the operator may switch between views from the different viewing elements manually). Alternatively, these video streams may be processed by the main control unit 199 to combine them into a single, panoramic video frame, based on an overlap between fields of view of the viewing elements. In an embodiment, two or more displays may be connected to the main control unit 199, each for displaying a video stream from a different viewing element of the multi-viewing element endoscope 102. The main control unit 199 is described in U.S. patent application Ser. No. 14/263,896, entitled "Method and System for Video Processing in a Multi-Viewing Element Endoscope" and filed on Apr. 28, 2014, which is herein incorporated by reference in its entirety.

Figure 2:
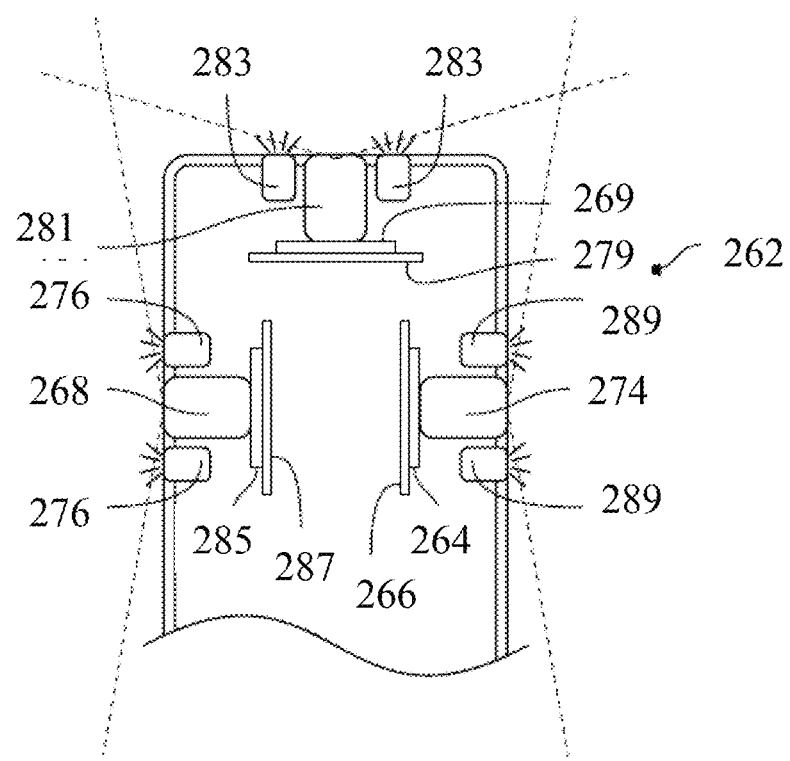
FIG. 2 is a cross-sectional view of a tip section of a multiple viewing element endoscope.

Reference is now made to FIG. 2, which shows a cross-sectional view of a tip section 262 of a multi-viewing element endoscope, according to another embodiment of the specification. Tip section 262 may include a front-pointing image sensor 269, such as a Complementary Metal Oxide Semiconductor (CMOS) image sensor. Front-pointing image sensor 269 may be mounted on an integrated circuit board 279, which may be rigid or flexible. Integrated circuit board 279 may be employed to supply front-pointing image sensor 269 with the necessary electrical power and may derive still images and/or video feeds captured by the image sensor. Integrated circuit board 279 may be connected to a set of electrical cables which may be threaded through an electrical channel running through the elongated shaft of the endoscope. Front-pointing image sensor 269 may have a lens assembly 281 mounted on top of it for providing the necessary optics for receiving images.

Lens assembly 281 may include a plurality of lenses, static or movable, which may provide a field of view of at least 90 degrees and up to essentially 180 degrees. In one embodiment, lens assembly 281 may provide a length over which an object remains in focus of about 3 to 100 millimeters. It should be appreciated that the term focal length may be used to refer to the distance from a lens to a sensor or may be used to refer to the distance, from the lens, over which an object remains in focus. One of ordinary skill in the art would understand what definition for focal length is being used based on the context and distances discussed.

Front-pointing image sensor 269 and lens assembly 281, with or without integrated circuit board 279, may be jointly referred to as a "front-pointing camera". One or more discrete front illuminators 283 may be placed next to lens assembly 281, for illuminating its field of view. In an alternate embodiment, discrete front illuminators 283 may also be attached to the same integrated circuit board 279 upon which front-pointing image sensor 269 is mounted.

Tip section 262 may optionally include, in addition to a first side-pointing image sensor 285, a second side-pointing image sensor 264. While FIG. 2 is discussed herein with respect to an embodiment with two side-pointing image sensors, it should be understood to those of ordinary skill in the art, that, in some embodiments, only one side pointing image sensor may be used.

Referring back to FIG. 2, side-pointing image sensors 285 and 264 may include a Complementary Metal Oxide Semiconductor (CMOS) image sensor. Side-pointing image sensors 285 and 264 may be mounted on integrated circuit boards 287 and 266, respectively, which may be rigid or flexible. Integrated circuit boards 287 and 266 supply side-pointing image sensors 285 and 264 with the necessary electrical power and derive still images and/or video feeds captured by the image sensor. Integrated circuit boards 287 and 266 are connected to a set of electrical cables (not shown) which may be threaded through an electrical channel running through the elongated shaft of the endoscope.

In another embodiment, side-pointing image sensors 285 and 264 receive the necessary electrical power from one integrated circuit board adapted to supply the necessary electrical power to both the sensors.

Side-pointing image sensors 285 and 264 have lens assemblies 268 and 274, respectively, mounted thereto for providing the necessary optics for receiving images. Lens assemblies 268 and 274 may include a plurality of lenses, static or movable, which provide a field of view of at least 90 degrees and up to essentially 180 degrees. Side-pointing image sensors 285 and 264 and lens assemblies 268 and 274, with or without integrated circuit boards 287 and 266, respectively, may be jointly referred to as a "side-pointing cameras".

Discrete side illuminators 276 and 289 may be placed next to lens assemblies 268 and 274, respectively, for illuminating its field of view. Optionally, in an alternate embodiment, discrete side illuminators 276 and 289 may be attached to the same integrated circuit boards 287 and 266 on which side-pointing image sensors 285 and 264 are mounted.

In another configuration, integrated circuit boards 279, 287, and 266 may be a single integrated circuit board on which front and side-pointing image sensors 269, 285, and 264, respectively, are mounted.

Front and side-pointing image sensors 269, 285, and 264 may be similar, identical or distinct in terms of, for example, field of view, resolution, light sensitivity, pixel size, focal length, focal distance and/or the like.

Figure 3:
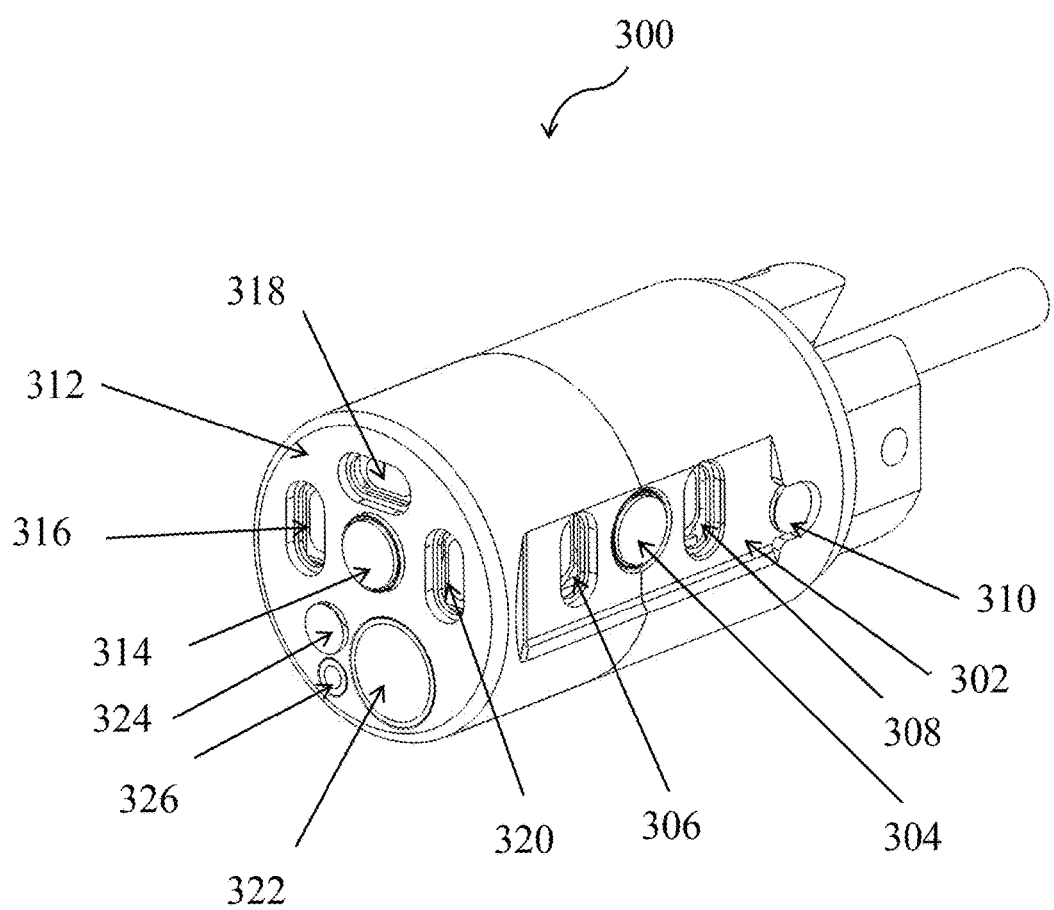
FIG. 3 illustrates an outer design of the tip of an endoscope, in accordance with an embodiment.

FIG. 3 illustrates the outer design of the tip of an endoscope, in accordance with an embodiment. Referring to FIG. 3, a side panel 302 is positioned on a side of the endoscope tip 300. The side panel 302 comprises an outer optical window 304, transparent surfaces, windows, optical windows or openings 306, 308, and a side nozzle 310. The outer optical window 304 is positioned on the circumference of the endoscope tip at a distance ranging from approximately 1 to 15 millimeters from the surface of the tip 300, and in an embodiment is positioned at approximately 7.0 or 9.0 millimeters, from the surface of the tip 300.

A front panel 312 is positioned on a front end of the endoscope tip 300. The front panel 312 comprises an optical window 314, transparent surfaces, windows, optical window or openings 316, 318, 320, a working/service channel opening 322, a nozzle opening 324 and a jet opening 326. In one embodiment, the diameter of the front working/service channel ranges from approximately 2.8 to 5.8 millimeters.

It may be noted that a base board, which in one embodiment is an electronic circuit board/printed circuit board, is associated with a fluid channeling component and adapted to support the optical assembly and illuminators of an endoscope. Thus, tip section of the endoscope may include a tip cover, an electronic circuit board assembly and a fluid channeling component. According to some embodiments, fluid channeling component may be configured as a separate component from electronic circuit board assembly. This configuration may be adapted to separate the fluid channels, such as a side service channel, and at least one front working/service channel, which are located in fluid channeling component, from the sensitive electronic and optical parts which may be located in the area of electronic circuit board assembly. Thus, the component structure of the tip section enables effective isolation of the plurality of electronic elements from the plurality of fluid channels.

A particular challenge arises when attempting to package the tip cover, electronic circuit board assembly and fluid channeling component such that they fit within the minimalistic space available inside the tip section, while still providing the required results. Thus, a significant problem exists in the art when attempts are made to pack all necessary components into the small inner volume of the endoscope. This problem dramatically increases when two or more viewing elements and respective illumination sources (such as LEDs) are packed in the tip of the endoscope.

Figure 4:
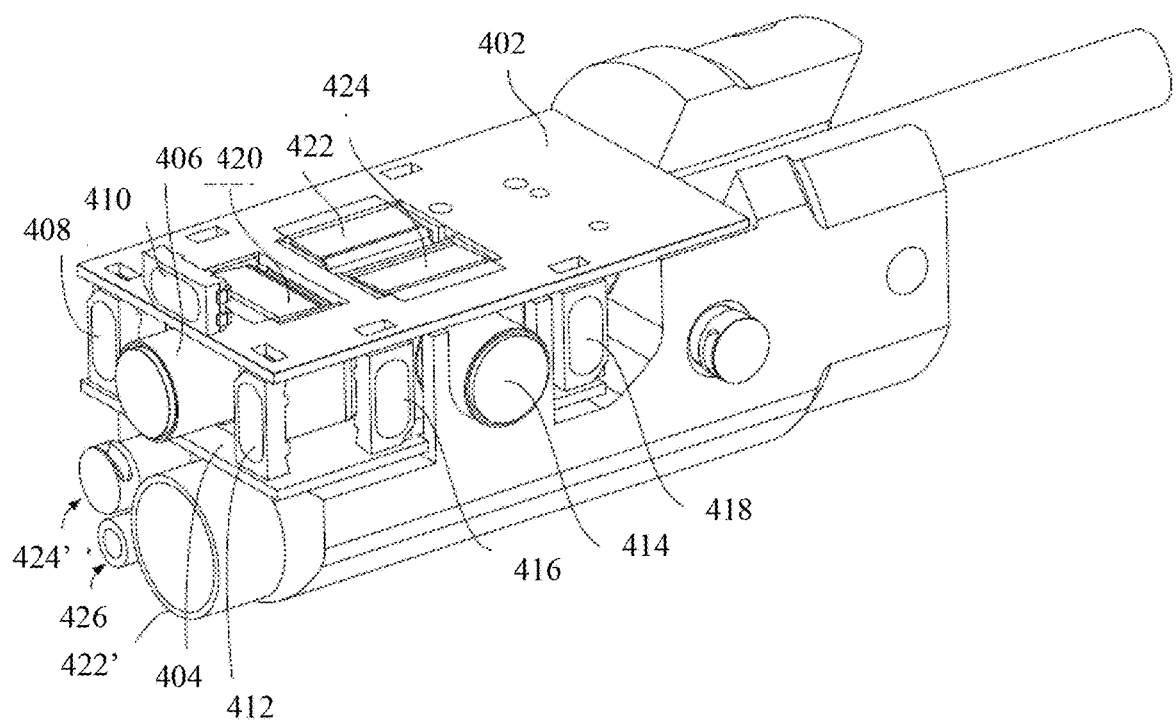
FIG. 4 illustrates a configuration of an endoscope tip where two base boards are used to support an optical assembly and illuminators.

FIG. 4 illustrates a configuration of an endoscope tip where two base boards are used to support the optical assembly and illuminators, where CCD sensors are employed. Referring to FIG. 4, an upper base board 402 and a lower base board 404 in combination, form an electronic circuit board/printed circuit board and support the optical assembly and illuminators. The front optical assembly comprises a front lens assembly 406 and a front image sensor, typically a CCD sensor. The side optical assembly comprises a side lens assembly 414 and a side image sensor, typically a CCD sensor. The front image sensor's connector pins and contact area 420 are manipulated, including being cut, bent or folded, to be soldered to the upper base board 402 and lower base board 404. The side image sensors' connector pins and contact areas 422 and 424 (for the right and left side image sensors, respectively) are bent to be soldered to the upper base board 402 and lower base board 404. The upper base board 402 and the lower base board 404 have grooves/holes enabling the front and side illuminators to be placed within the grooves/holes. The upper and lower base boards 402, 404 hold three sets of front illuminators 408, 410, 412 and on each side panel two sets of illuminators 416, 418 (the figure illustrates only one first side panel of the endoscope, however it should be understood by those of ordinary skill in the art that the second side panel is equivalent to this side panel). Front illuminators 408, 412 are placed between the upper and lower base boards 402, 404, while front illuminator 410 is placed above front lens assembly 406. The two sets of illuminators 416, 418 are placed between the upper and lower base boards 402, 404.

As shown in FIG. 4, jet opening 426 and nozzle opening 424' may be positioned adjacent to each other on front panel of the tip. Alternately, the openings may be positioned on either side of the working/service channel opening 422' on the front panel of the tip.

In order to make more efficient use of the limited space available within the tip, in embodiments of the present specification, a CMOS sensor is employed in a novel circuit board design that eliminates the need of having two base boards (the upper base board 402 and lower base board 404) as described above. By reducing the number of base boards required from two to one, the present specification offers a more efficient design for the tight architecture of the distal tip of an endoscope.

Figure 5:
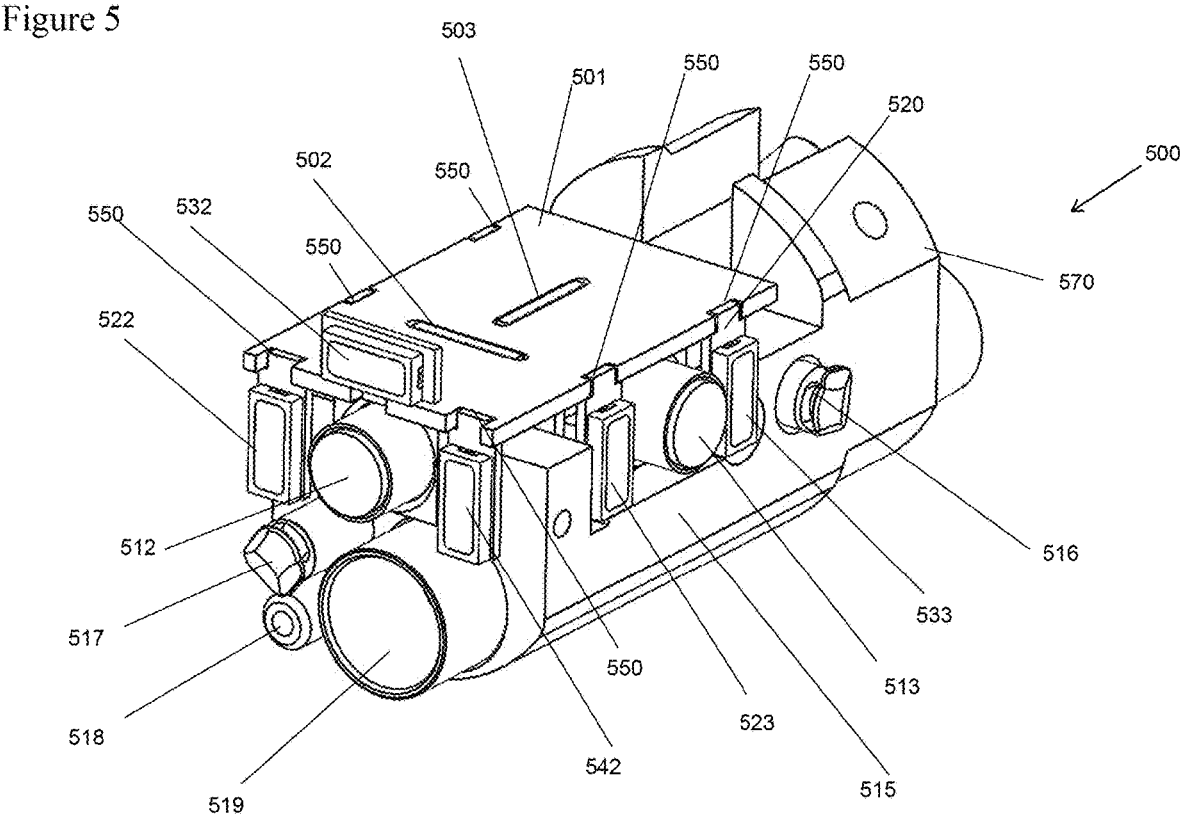
FIG. 5 illustrates a base board assembly with CMOS sensors, according to one embodiment of the present specification.

FIG. 5 illustrates one embodiment of a base board assembly for housing CMOS sensors-based components. Referring to FIG. 5, a base board 501 is associated with a fluid channeling component 570 and is adapted to support the optical assembly and illuminators in an endoscope tip 500. In one embodiment, base board 501 comprises grooves 502 and 503, in which two smaller sections of the baseboard, also referred to as sensor base boards may be placed. A first sensor base board section houses a front sensor and may be placed into groove 502 while a second sensor base board section houses at least one side sensor and is placed into groove 503.

In various embodiments, the base board 501 is provided with grooves/holes 550 for the front illuminators 522, 532, 542 and for the first set of side illuminators 523, 533 and the second set of side illuminators (not shown) to be placed within. In one embodiment grooves 550 are identical for all illuminators, while in another embodiment each of the grooves may be adapted for different sizes of illuminators. For example, different types of illuminators may comprise LEDs (Light Emitting Diode) adapted to emit white light, infrared light, ultraviolet light, near-infrared light and other wavelengths of light and each type of illuminator may have a different size.

In one embodiment, a separate circuit board, such as circuit board 520 (described in greater detail with respect to FIG. 7 as 720), may be provided to hold each of the illuminators. Thus, for example in an endoscope tip having seven (7) illuminators, three on the front and two on each side, seven (7) separate circuit boards adapted to hold the seven illuminators may be provided. Circuit board 520 is coupled to the base board 501. The side optical assembly, comprising side lens assembly 513 and side illuminators 523 and 533 is placed in a side panel 515, which also houses a side nozzle 516. At the front of the endoscope tip is a nozzle opening 517, a jet opening 518 and a working/service channel opening 519, which have been described earlier with reference to FIG. 3.

Figure 6A:
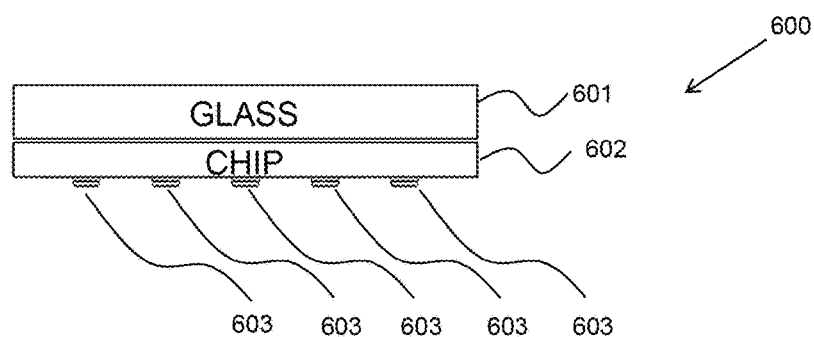
FIG. 6a is a side view of an exemplary CMOS image sensor comprising an image sensor contact area, in accordance with an embodiment of the present specification.
Figure 6B:
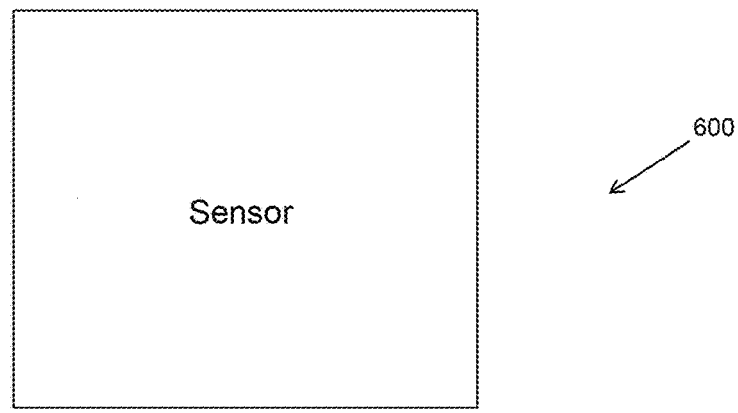

As mentioned above, the front sensor and the side sensors in the present embodiment comprise CMOS sensors, which can be connected to an electronic board with ease and simplicity. FIG. 6b illustrates a front looking view of a CMOS image sensor 600, while FIG. 6a illustrates a side view of the same image sensor shown in FIG. 6b. Referring to FIG. 6a, CMOS image sensor 600 is equipped with a plurality of connector pins 603. The image sensor 600 also includes piece of glass or an optics portion 601 and a printed circuit board or computer chip 602. Since the glass optics portion 601 of the image sensor 600 is associated with the lens assembly, it is always placed to face away from a center of the endoscope tip and towards an object to be viewed. Therefore, when integrating with the baseboard of an endoscope tip, the optics portion 601 of the CMOS sensor 600 is directed towards the lens assembly of the endoscope tip, while the printed circuit board or integrated circuit portion 602 of the CMOS sensor 600 is connected to a sensor base board by means of pins 603 on the printed circuit board.

Figure 7:
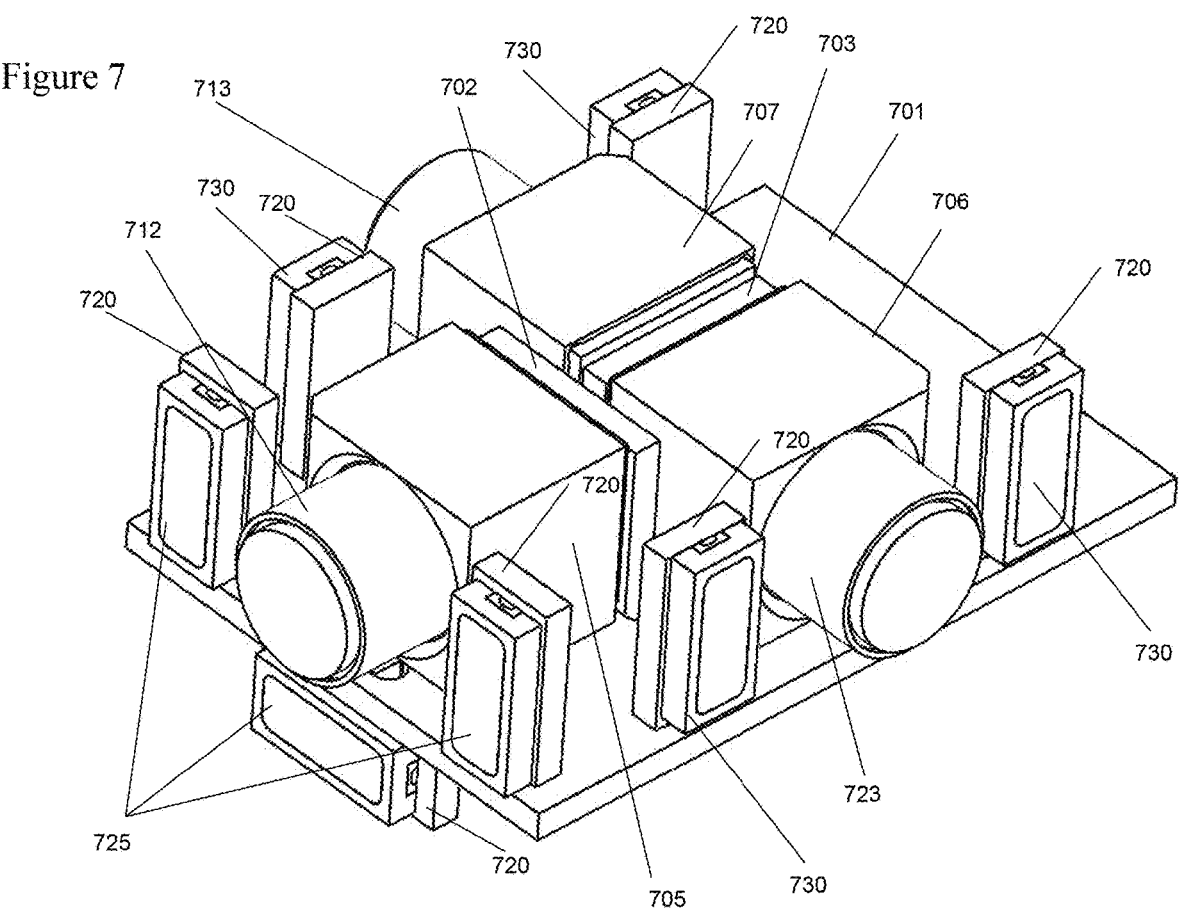
FIG. 7 is a bottom view of a base board adapted to support the optical assembly and illuminators of an endoscope, according to one embodiment.

FIG. 7 illustrates a view of one embodiment of a base board adapted to support the optical assembly and illuminators of an endoscope. Referring to FIG. 7, the base board assembly comprises a main base board 701, which is associated with two smaller baseboards—the front sensor base board 702 and a side sensor base board 703. In one embodiment, the front sensor base board 702 and the side sensor base board 703 are placed perpendicular to each other. In one embodiment, the front sensor base board 702 and the side sensor base board 703 are also placed perpendicular to the main base board 701, in a three dimensional space. The front sensor base board 702 carries the front sensor and the front lens assembly 712. The side sensor base board 703 carries two side sensors and their associated side lens assemblies 713 and 723. It may be noted that by placing the side sensors and lens assemblies on either side of the side sensor base board 703, the side sensors are able to share one board, thereby saving space in the endoscope tip.

In an alternate embodiment, the front sensor base board 702 carries the front sensor and the front lens assembly 712, while the side sensor base board 703 carries only one side sensor and its associated side lens assembly 713 or 723.

In one embodiment, both the front and the side base boards are coupled to metal frames 705, 706, 707 which are positioned to support and hold the front and side lens assemblies 712, 713 and 723, respectively. In an embodiment, metal frames 705, 706, 707 also serve as heat sinks to the sensors incorporated in the endoscope. In one embodiment, as mentioned with respect to FIG. 5 above, a separate circuit board 720 is provided to hold each illuminator, including the front illuminators 725 and side illuminators 730. The illuminator circuit boards 720 are coupled to the main base board 701 by means of grooves/holes (shown in FIG. 5) made in the main base board 701.

It may be noted that in alternate, optional designs of the base board, such as the one shown and explained with reference to FIG. 4 which comprises an upper base board and a lower base board, a metal supporting frame may be placed between the viewing element holders. The metal supporting frame supports the viewing element holders by fixedly placing them between the upper and lower base boards. In some embodiments, the metal supporting frame is equipped with an internal air or fluid channel such that it acts as heat sink for the illuminators. In some designs, the metal supporting frame may also be integrated with the optical assemblies and acts as a heat sink for the LEDs while supporting the optical assemblies to be fixedly placed between the upper and lower base boards.

FIG. 8 illustrates another perspective view of the circuit board design of the present specification. Referring to FIG. 8, a side sensor base board 801 is connected to two side image sensors 802 and 803, which are CMOS sensors in the present embodiment. The CMOS sensors 802, 803 (similar to CMOS sensor 600 shown in FIG. 6a) are integrated with the side sensor base board by directing the optics portion (such as glass portion 601 shown in FIG. 6a) of the sensors towards the lens assembly of the endoscope tip, and connecting the pins 812, 813 (similar to pins 603 shown in FIG. 6a) of the printed circuit board (such as chip portion 602 shown in FIG. 6a) or computer chip of the sensors to the side sensor base board. By connecting two side image sensors 802 and 803 to one side sensor base board 801, the side sensors 802, 803 are able to share one board 801, thereby saving space in the endoscope tip. The side sensor board 801 is also connected to the main base board 810. In one embodiment, the side sensor board 801 is placed perpendicular to the main base board 810.

FIG. 9 illustrates another exemplary embodiment for assembling CMOS sensors to a base board in an endoscope tip, wherein each image sensor connects to a dedicated board. Referring to FIG. 9, a first side sensor 901 is connected to a first side sensor base board 911 and a second side sensor 902 is connected to a second side sensor base board 912. The circuit board assembly further comprises a front image sensor 903, which is connected to a dedicated front sensor base board 913. Side image sensors 901 and 902 and the front image sensor 903, are CMOS sensors in the present embodiment. The CMOS sensors are integrated with their respective sensor base boards by directing the optics part of the sensors, such as portions 903a and 902a of sensors 902 and 903 respectively, towards the lens assembly (not shown) of the endoscope tip, and connecting the pins (not shown in FIG. 9) of the printed circuit board or computer chip of the sensors to their dedicated sensor base board. The side sensor boards 911, 912 and the front sensor base board 913 are also connected to the main base board 910. In one embodiment, each of the side sensor boards 911 and 912 and the front sensor base board 913 are connected to main base board 910 by means of a dedicated flexible circuit board or flex board. As shown in the figure, flex board 923 connects between the front base board 913 and the main base board 910. Similarly, flex board 922 is adapted to connect between the side base board 912 and the main base board 910. Side base board 911 is connected to the main base board by another flex board (not shown). It may be appreciated that any flexible boards known in the art that are suitable for the application may be used in the present embodiment.

It may be noted that use of a flex board is advantageous in a multi-viewing element endoscope, owing to shortage of space in the tip exacerbated by the presence of multiple viewing elements. The flex board provides additional freedom of movement to the assembly process in a space constrained environment, and allows the two side sensor boards 911, 912 to be aligned in parallel and as close as possible one to each other. In one embodiment, side sensor base boards 911 and 912 are placed parallel to each other, while being placed perpendicular to the main base board 910. The front base board 913 is placed perpendicular to the side base boards 911 and 912, and also perpendicular to the main base board 910.

Figure 10:
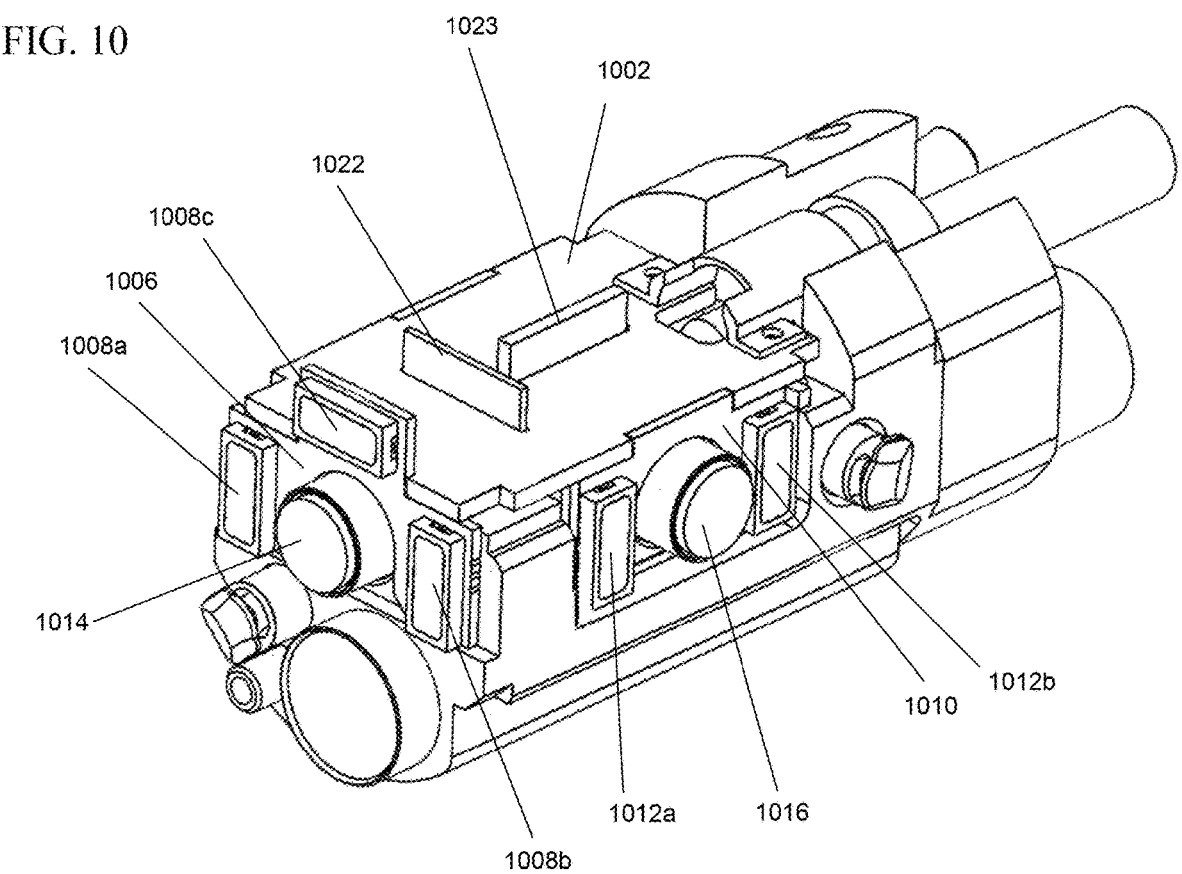
FIG. 10 illustrates another base board assembly with CMOS sensors, according to one embodiment of the present specification.

FIG. 10 illustrates a front illuminator electronic circuit board 1006 adapted for supporting the front illuminators 1008a, 1008b, 1008c of an endoscope, in accordance with another embodiment of the present specification. FIG. 10 also illustrates a main base board 1002 and a side illuminator electronic circuit board 1010 for supporting the side illuminators 1012a, 1012b (also as shown earlier in FIG. 3). The front illuminators 1008a, 1008b, 1008c are associated with a front optical assembly comprising a front lens assembly 1014 and a front image sensor. The side illuminators 1012a, 1012b are associated with a side optical assembly comprising a side lens assembly 1016 and a side image sensor. The front sensor base board 1022 and side sensor base board 1023 are soldered to respective grooves (shown in FIG. 5) placed in the main base board 1002. On each side panel, a side illuminator electronic circuit board 1010 holds a set of side illuminators 1012a, 1012b (the figure illustrates only one side panel of the endoscope, however it should be understood by those of ordinary skill in the art that the other side panel is equivalent to the shown side panel). In one embodiment, front illuminators 1008a, 1008b are positioned on either side of the front lens assembly 1014 while front illuminator 1008c is positioned above front lens assembly 1014 and above the main base board 1002. The two illuminators 1012a, 1012b on both sides of the endoscope tip are positioned on either side of the side lens assembly 1016. In various embodiments, any material that is used for constructing a PCB (printed circuit board) may be used for constructing the front and side illuminator circuit boards. Typical materials used for making PCB boards are ceramic, polyamides for flexible board, and glass-reinforced epoxy, such as, FR4 (a composite material composed of woven fiberglass cloth with an epoxy resin binder that is flame resistant (self-extinguishing)). Also in various embodiments, the front and side illuminator circuit boards may or may not be made of the same materials as the upper and lower base boards.

Figure 11:
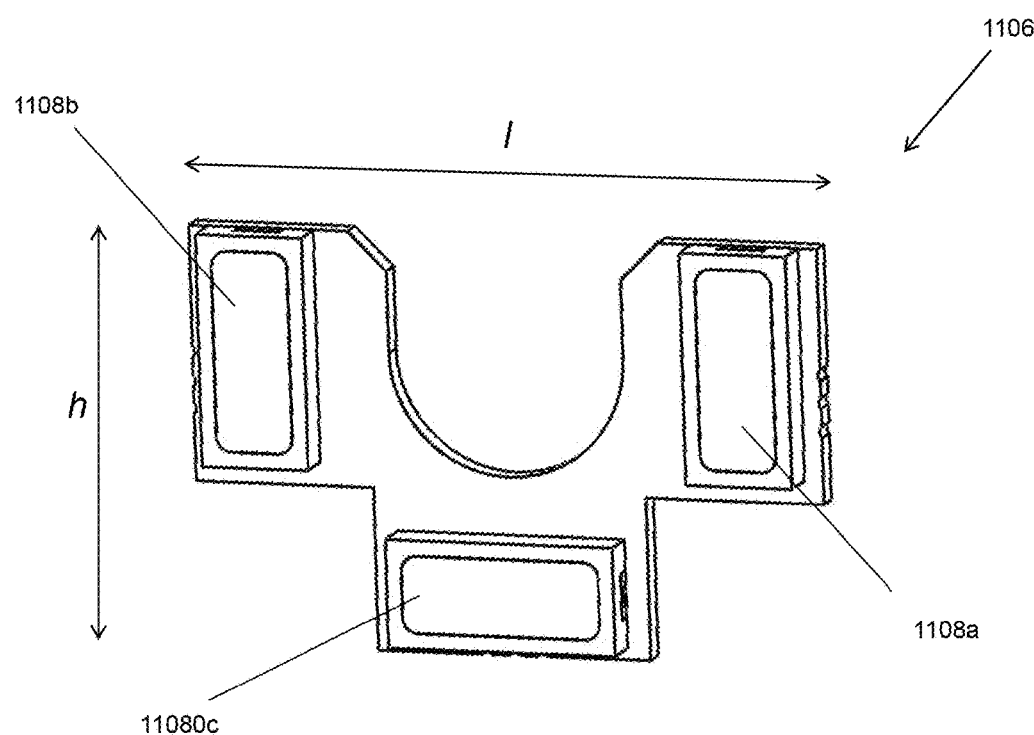
FIG. 11 illustrates front illuminators on a substrate, in accordance with an embodiment of the present specification.

FIG. 11 illustrates a front illuminator electronic circuit board 1106, in accordance with an embodiment of the present specification. In one embodiment, as depicted in FIG. 11, the circuit board 1106 is shaped as a 'U' and holds front illuminators 1108a, 1108b, 1108c in place. In various embodiments, the length l of the front illuminator electronic circuit board 1106 ranges from 5.5 mm to 11.5 mm, preferably 7.5 mm to 9.5 mm, and in an embodiment the length l is approximately 6.0 to 11.0 mm, preferably 8.0 to 9.0 mm. In various embodiments, the height h of the front illuminator electronic circuit board 1106 ranges from 2.0 mm to 8.5 mm, preferably 4.0 mm to 6.5 mm, and in an embodiment the height h is approximately 3.0 mm to 8.0 mm, preferably 5.0 to 6.0 mm.

Figure 12:
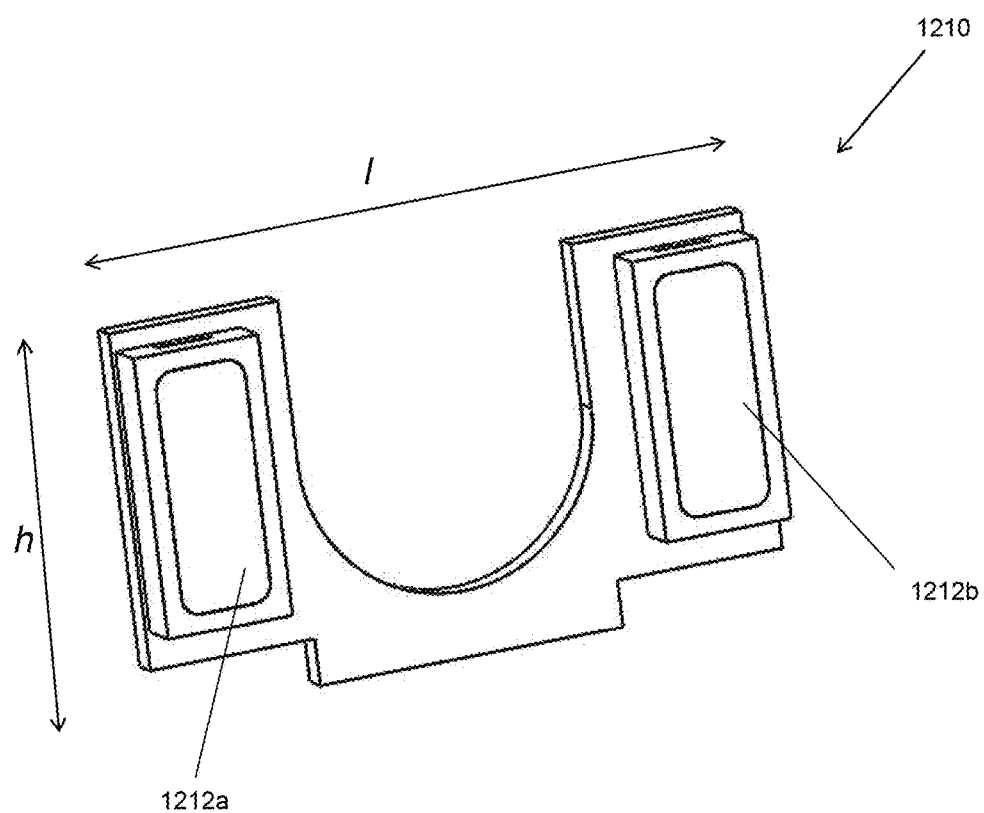
FIG. 12 illustrates side illuminators on a substrate, in accordance with an embodiment of the present specification.

FIG. 12 illustrates a side illuminator electronic circuit board 1210, in accordance with an embodiment of the present specification. In one embodiment, as depicted in FIG. 12, the circuit board 1210 is shaped as a 'U' and holds side illuminators 1212*a*, 1212*b* in place. In various embodiments, the length l of the side illuminator electronic circuit board 1210 ranges from 5.5 mm to 11.5 mm, preferably 7.5 mm to 9.5 mm, and in an embodiment the length l is approximately 4.5 to 9.5 mm, preferably 6.5 to 7.5 mm. In various embodiments, the height h of the front illuminator electronic circuit board 1106 ranges from 1.0 mm to 7.5 mm, preferably 3.0 mm to 5.5 mm, and in an embodiment the height h is approximately 2.0 mm to 7.0 mm, preferably 3.7 to 4.7 mm.

Figure 13:
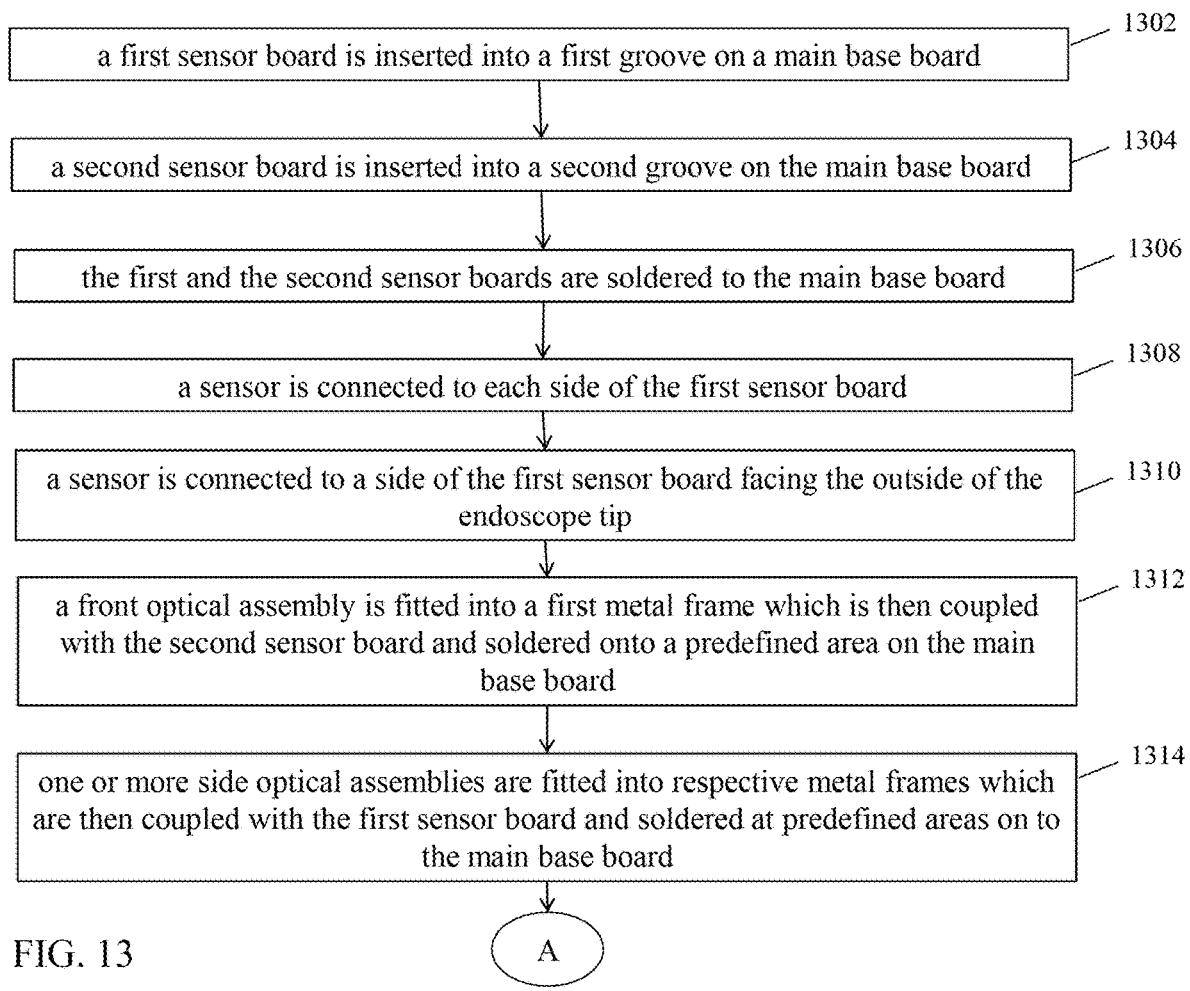
FIG. 13 is a flowchart illustrating the steps of assembling front and side optical assemblies and sensors in an endoscope tip, in accordance with an embodiment of the present specification.

FIG. 13 is a flowchart illustrating the steps of assembling front and side optical assemblies and sensors in an endoscope tip, in accordance with an embodiment of the present specification. At step 1302, a first sensor board is inserted into a first groove on a main base board. In one embodiment, the first sensor board is used for holding one or more side sensors and is placed perpendicular to the main base board. At step 1304, a second sensor board is inserted into a second groove on the main base board. In one embodiment, the second sensor board is used for holding a front sensor and is placed perpendicular to the main base board as well as to the first sensor board. At step 1306, the first and the second sensor boards are soldered to the main base board. In an embodiment, the first and the second sensor boards are connected to the main base board by using one or more flex boards. At step 1308, a sensor is connected to each side of the first sensor board. At step 1310, a sensor is connected to a side of the first sensor board facing the outside of the endoscope tip. In an embodiment, the sensor is a CMOS sensor which is connected to a sensor board by directing optics part of the sensor towards a lens assembly of the endoscope tip, and connecting the pins of the computer chip of the sensor to the sensor board. At step 1312 a front optical assembly is fitted into a first metal frame which is then coupled with the second sensor board and soldered onto a predefined area on the main base board. At step 1314 one or more side optical assemblies are fitted into respective metal frames which are then coupled with the first sensor board and soldered at predefined areas on to the main base board. At step 1316 two or more illuminators are fitted to respective front illuminator boards which are inserted into corresponding front illuminator grooves in the main base board. At step 1318 the front illuminator boards are soldered to the main base board. At step 1320 two or more illuminators are fitted to respective side illuminator boards which are inserted into corresponding side illuminator grooves in the main base board. At step 1322 the side illuminator boards are soldered to the main base board.

In one embodiment, the circuit board assembly of the present specification can also be adapted for use with CCD sensors. That is, the same circuit board is designed as a common platform that can support either of the two technologies—CCD or CMOS, depending upon the application and requirement.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An electronic assembly for an endoscope comprising:
   a front pointing image sensor and a first side pointing image sensor; and
   a circuit board assembly comprising:
      a first rigid base board to which the front pointing image sensor is connected;
      a second rigid base board, wherein the first side pointing image sensor is connected to a first side of the second rigid base board; and
      a third rigid base board to which the first rigid base board and the second rigid base board are connected, wherein the first rigid base board and the second rigid base board are placed transverse to the third rigid base board;
      a first flexible circuit board connecting the first rigid base board to the third rigid base board; and
      a second flexible circuit board connecting the second rigid base board to the third rigid base board;
   wherein the first flexible circuit board extends from a first edge of the first rigid base board to a second edge of the third rigid base board;
   wherein the second flexible circuit board extends from a third edge of the second rigid base board to a fourth edge of the third rigid base board, wherein the fourth edge is substantially perpendicular to the second edge;
   wherein the front pointing image sensor and the circuit board assembly are configured to be received within a tip of the endoscope; and
   wherein each of the first rigid base board and the second rigid base board is configured to be moveable relative to the third rigid base board.

2. The electronic assembly of claim 1, wherein the first rigid base board is positioned entirely distal to the third rigid base board.

3. The electronic assembly of claim 1, further comprising a fourth rigid base board, wherein a third side pointing image sensor is connected to the fourth rigid base board.

4. The electronic assembly of claim 3, wherein a third flexible circuit board connects the fourth rigid base board to the third rigid base board.

5. The electronic assembly of claim 1, further comprising a first illuminator circuit board including a first illuminator; and a second illuminator circuit board including a second illuminator, wherein the first illuminator circuit board has a length ranging from 5.5 mm to 11.5 mm and a height ranging from 2.0 mm to 8.5 mm.

6. The electronic assembly of claim 5, wherein the third rigid base board includes a first groove at a distalmost end of the third rigid base board configured to receive the first illuminator circuit board.

7. The electronic assembly of claim 5, wherein the second illuminator circuit board is positioned within a second groove at a distalmost end of the third rigid base board.

8. The electronic assembly of claim 5, wherein the first illuminator circuit board is adjacent to the front pointing image sensor; and wherein the second illuminator circuit board is adjacent to the front pointing image sensor and on an opposing side of the front pointing image sensor as the first illuminator circuit board.

9. The electronic assembly of claim 5, wherein the second illuminator is positioned on an opposite side of the third rigid base board as the first illuminator.

10. The electronic assembly of claim 6, wherein the second illuminator circuit board is received within a second groove of the third rigid base board, and wherein the first groove and the second groove are positioned on an edge of the third rigid base board.

11. An electronic assembly for an endoscope comprising:
a first side pointing image sensor; and
a circuit board assembly comprising:
- a first base board;
- a second base board, wherein the first side pointing image sensor is connected to a first side of the second base board;
- a third base board to which said first and said second base boards are connected, wherein the first base board and the second base board are placed transverse to the third base board;
- a fourth base board including a first groove, wherein a portion of the first base board is received within the first groove;
- a first flexible circuit board connecting the first base board to the third base board, wherein the first flexible circuit board extends from a first side surface of the first base board to a second side surface of the third base board, wherein the first side surface faces a direction transverse from a central longitudinal axis of the endoscope, and wherein the second side surface faces a distal direction; and
- a second flexible circuit board connecting the second base board to the third base board, wherein the second flexible circuit board extends from a third side surface of the second base board to a fourth side surface of the third base board, wherein each of the third side surface and the fourth side surface faces a direction transverse from the central longitudinal axis of the endoscope;
- wherein the first side pointing image sensor and the circuit board assembly are configured to be received within a tip of the endoscope; and
- wherein the first base board and the second base board are configured to be moveable relative to the third base board.

12. The electronic assembly of claim 11, further comprising:
- a first illuminator circuit board including only one illuminator; and
- a second illuminator circuit board including only one illuminator;
- wherein the third base board includes 1) a first groove at a distalmost end of the third base board configured to receive the first illuminator circuit board and 2) a second groove at a distalmost end of the third base board configured to receive the second illuminator circuit board.

13. The electronic assembly of claim 11, further comprising a fluid channeling component including at least one fluid channel and a side panel configured to receive the first side pointing image sensor.

14. The electronic assembly of claim 11, further comprising a fourth base board, wherein a second side pointing image sensor is connected to the fourth base board.

15. The electronic assembly of claim 11, wherein the first side surface faces a first direction, and the third side surface faces the first direction.

16. The electronic assembly of claim 15, wherein the second side surface is substantially perpendicular to the fourth side surface.

17. An electronic assembly for an endoscope comprising:
a front pointing image sensor;
a first side pointing image sensor; and
a circuit board assembly comprising:
- a first base board, wherein the front pointing image sensor is connected to the first base board;
- a second base board, wherein the first side pointing image sensor is connected to the second base board;
- a third base board to which the first base board and the second base board are connected;
- a first flexible circuit board connecting the first base board to the third base board, wherein the first base board is positioned entirely distal from the third base board, wherein the first flexible circuit board extends from a first side surface of the first base board to a second side surface of the third base board, and wherein the second side surface faces a distal direction; and
- a second flexible circuit board connecting the second base board to the third base board;
- wherein the front pointing image sensor, the first side pointing image sensor, and the circuit board assembly are configured to be received within a tip of the endoscope; and
- wherein the first base board and the second base board are configured to be moveable relative to the third base board.

18. The electronic assembly of claim 17, wherein the second flexible circuit board extends from a third side surface of the second base board to a fourth side surface of the third base board; and wherein a first longitudinal axis of the first side surface extends transverse from each of a second longitudinal axis of the second side surface and a third longitudinal axis of the third side surface.

19. The electronic assembly of claim 17, wherein the second flexible circuit board extends from a third side surface of the second base board to a fourth side surface of the third base board, and wherein the fourth side surface faces a first direction and the fourth side surface faces a second direction, and wherein the first direction is substantially perpendicular to the second direction.

* * * * *